(12) United States Patent
Blankenstein et al.

(10) Patent No.: US 9,383,293 B2
(45) Date of Patent: Jul. 5, 2016

(54) DEVICE FOR PLASMA SEPARATION BY MEANS OF A CENTRAL CHANNEL STRUCTURE

(75) Inventors: Gert Blankenstein, Arlington, MA (US); Thanh Tu Hellmich-Duong, Jena (DE); Dirk Kurowski, Gevelsberg (DE); Dirk Osterloh, Unna (DE)

(73) Assignee: Boehringer Ingelheim Microparts GmbH, Dortmund (DE)

( * ) Notice: Subject to any disclaimer, the term of this patent is extended or adjusted under 35 U.S.C. 154(b) by 494 days.

(21) Appl. No.: 13/640,393

(22) PCT Filed: Apr. 1, 2011

(86) PCT No.: PCT/EP2011/055078
§ 371 (c)(1),
(2), (4) Date: Jan. 10, 2013

(87) PCT Pub. No.: WO2011/131471
PCT Pub. Date: Oct. 27, 2011

(65) Prior Publication Data
US 2013/0112612 A1    May 9, 2013

(30) Foreign Application Priority Data

Apr. 23, 2010    (EP) .................................. 10160817

(51) Int. Cl.
*G01N 1/28* (2006.01)
*B01L 3/00* (2006.01)
(Continued)

(52) U.S. Cl.
CPC .............. *G01N 1/28* (2013.01); *B01L 3/50273* (2013.01); *B01L 3/502723* (2013.01);
(Continued)

(58) Field of Classification Search
CPC ... B01L 3/00; B01L 3/5027; B01L 3/502746; B01L 3/50273; B01L 3/502753; B01L 2300/0681; B01L 2300/0851; B01L 2300/087; B01L 2300/0887; B01L 2300/027; G01N 33/49; G01N 33/50; G01N 1/28; G01N 33/491
See application file for complete search history.

(56) References Cited

U.S. PATENT DOCUMENTS

| 4,906,439 A | 3/1990 | Grenner |
| 7,736,907 B2 | 6/2010 | Blankenstein et al. |

(Continued)

FOREIGN PATENT DOCUMENTS

| CA | 2293019 A1 | 6/2000 |
| EP | 0597577 A1 | 5/1994 |

(Continued)

OTHER PUBLICATIONS

International Search Report, Form PCT/ISA/210, for corresponding PCT/EP2011/055078; date of mailing: May 23, 2011.

(Continued)

*Primary Examiner* — Katherine Zalasky
*Assistant Examiner* — Benjamin Lebron
(74) *Attorney, Agent, or Firm* — Michael P. Morris; Mary-Ellen M. Devlin

(57) ABSTRACT

The invention relates to a device for sample separation, particularly for blood separation, in which the sample liquid is introduced into a feed device. The sample flows vertically through a separating device such as a filter or a membrane, so that sample particles are retained and separated off.
The sample liquid thus separated, particularly blood plasma, is received by an inlet chamber underneath the separating device and conveyed by means of a channel in the lateral direction out of the inlet chamber.
Particularly advantageously, the channel extends into the inlet chamber, the channel being formed by a recess in the base of the inlet chamber.

12 Claims, 5 Drawing Sheets

(51) Int. Cl.
*G01N 33/49* (2006.01)
*B29C 65/54* (2006.01)

(52) U.S. Cl.
CPC ........ *G01N 33/491* (2013.01); *B01L 3/502715* (2013.01); *B01L 3/502746* (2013.01); *B01L 3/502753* (2013.01); *B01L 2200/027* (2013.01); *B01L 2300/0681* (2013.01); *B01L 2300/087* (2013.01); *B01L 2300/0851* (2013.01); *B01L 2300/0887* (2013.01); *B01L 2400/0406* (2013.01); *B29C 65/548* (2013.01); *G01N 33/492* (2013.01)

(56) References Cited

U.S. PATENT DOCUMENTS

| | | | |
|---|---|---|---|
| 2004/0228770 A1* | 11/2004 | Gandhi et al. | 422/102 |
| 2006/0008381 A1* | 1/2006 | Taguchi | B01L 3/5027 422/400 |
| 2007/0269893 A1 | 11/2007 | Blankenstein et al. | |
| 2008/0305008 A1* | 12/2008 | Hyland et al. | 422/68.1 |
| 2009/0120865 A1 | 5/2009 | Chung et al. | |

FOREIGN PATENT DOCUMENTS

| | | | | |
|---|---|---|---|---|
| EP | 1013341 | A2 | 6/2000 | |
| JP | 2005265685 | A | 9/2005 | |
| JP | 2008501938 | A | 1/2008 | |
| NL | WO 2011027262 | A1 * | 3/2011 | ........ B01L 3/502715 |
| WO | 2009075709 | A1 | 6/2009 | |
| WO | 2009110089 | A1 | 9/2009 | |
| WO | 2009112982 | A1 | 9/2009 | |

OTHER PUBLICATIONS

Abstract in English for JP2005265685, 2005.

* cited by examiner

DEVICE FOR PLASMA SEPARATION BY MEANS OF A CENTRAL CHANNEL STRUCTURE

The invention relates to a device for filtering a fluid and for conveying the filtered fluid, particularly plasma, into a diagnostic test cartridge.

The invention is used in microfluidic devices which are used for fluid separation, particularly blood separation.

In the separation of particles from a fluid, such as blood separation, for example, the medium that is to be separated, in this case blood, is added to a filter. The fluid and small ingredients pass through the filter and are transported away through channels in the device. In order to detect particular properties of the fluid, the fluid is brought into contact with reagents which bring about a chemically or physically detectable interaction, e.g. staining of the fluid in the case of a detection reaction.

For these different wet chemical, biochemical or diagnostic analyses it is essential to mix the fluid with reagents in a chamber or a reservoir for a defined period of time and thereby dissolve them and/or react with them.

The reagents may be bound to a chamber, a channel or a reservoir wall or to the surfaces of particles.

In immunochemical analyses, the reagents may be for example antibodies, enzymes, biotinylated proteins and antibodies, streptavidin or phosphatases.

In different solution or reaction processes of this kind it is necessary to provide a specific given flow volume or mass flow of fluid within a specified time interval in order to ensure that the reagent is dissolved or a reaction is reliably obtained.

If the required flow of fluid is insufficient or stops, there is the danger, for example, that components of a dried, particularly powdered, substance located in the microfluidic analysis equipment will clump together or be left behind as deposits. This may cause the results of a detection reaction to be falsified.

Also in applications where a plurality of chambers are to be filled in parallel or sequentially, a sufficient flow of fluid for homogeneously filling the chambers is essential.

For example the inclusion of air bubbles in the separation region or in the region of the entrance to a fluid-carrying channel is critical for the provision of a homogeneous supply of fluid to the detection chambers, as trapped air bubbles may reduce the flow volume or stop it altogether.

Against this background the problem underlying the invention is to provide a given amount of fluid that is to be investigated within a specified time interval in an examination region.

The invention is also based on the objective of designing the construction of a microfluidic device such that there is a reliable supply of the separated fluid from the entry region to the analysis region.

As adhesive coatings and also numerous plastics of the kind typically used in microfluidic cartridges are hydrophobic, these may prevent or obstruct the entry of aqueous liquids into a supply channel.

Against this background a further aim of the invention is to design the capillary aperture of a fluid discharge channel in its construction and/or function such that reliable wetting of the discharge channel is obtained, i.e. it must be ensured that the separated liquid can be accommodated by the discharge channel and transported away by it.

A separation device is known from EP 1548433 A1 in which the liquid that is to be separated is applied to a separation membrane through a feed opening and the filter process is carried out in the direction of thickness of the membrane. The filtered fluid is received in a fill chamber and conveyed away through capillary channels.

A disadvantage of this arrangement is the large dead volume in the fill chamber and the risk that any air contained in the chamber will not be displaced homogeneously by the fluid but will form air bubbles in the fluid that interfere with the flow of fluid.

By the dead volume is meant the volume of the fluidic channel structures and chambers that does not act as a reaction volume. As the fill chamber according to EP 1548433 A1 has to be totally filled to start with and fluid remains in the chamber, the chamber volume of the fill chamber is thus the dead volume.

EP 1 054 805 B1 describes a method for filling a microfluidic network from a central sample feed which has a cross-section of opening that has a capillary action. For transporting the sample away from the sample feed, which is in the form of an inlet chamber, a feed channel opens into a wall of the chamber. In order to improve the capillary sample reception through the feed channel, the capillary aperture of the feed channel is made larger by the fact that an encircling capillary chamber open to the inlet chamber is fluidically connected to the feed channel.

If a liquid comes into contact with this capillary channel or slot, the liquid automatically travels by capillary action into the microfluidic network if the contact angle of the liquid with the substrate and the viscosity of the liquid are not too high.

Again, a disadvantage of this arrangement is an increased dead volume in the arrangement, as the sample fluid separated may be held back by the encircling capillary channel.

Against this background the invention has the further aim of providing an improved separation device with a reduced dead volume.

These objectives are achieved according to the invention by a microfluidic device having the features of claim 1.

The microfluidic separation device according to the invention makes it possible to provide a sufficient volume flow of fluid. For this, the device has means for separation, particularly for filtering blood and comprises a discharge channel that receives and carries away the separated fluid. The device according to the invention makes it possible to fill a microfluidic network and/or a chamber from a discharge channel with a smaller active capillary cross-section or a small opening aperture. Moreover, using the method described, the dead space of a feed device and/or separating device can be reduced to a minimum.

In microfluidic cartridges as a rule the microfluidic network is formed by moulding in a plate-shaped substrate. Preferably a mouldable plastic such as polystyrene (PS), polymethyl methacrylate (PMMA), polycarbonate (PC), olefin polymers and olefin copolymers such as cycloolefin in polymer and cycloolefin in copolymer (COC and COP), polyamide (PA), polypropylene (PP), polyethylene (PE) or polyethylether ketone (PEEK) is injected into a negative mould.

Advantageously the channel structures are sealed off by a film arranged on the substrate.

The film covers the channel and/or chamber structures moulded into one or both sides of the plate, thus forming a microfluidic channel system with structures ranging in width and height from a few tens of microns to a few millimetres. The film covers the plate-shaped component partially or over its entire surface.

The film may be of multilayer construction. In particular the film may be provided on one or both sides with an adhesive layer for attaching to the plate-shaped substrate. The adhesive layer is preferably a low-melting laminated layer or sealing layer of ethylene-vinyl acetate copolymer (EVA). Alternatively the adhesive layer may also be an acrylate adhesive.

The surface and/or the channel structures may have been subjected to a surface treatment and/or surface coating over all or part of their surfaces. Examples of surface treatments or activations that may be carried out include plasma irradiation/plasma etching, gamma irradiation or UV irradiation for improving surface adhesion.

Surface coatings that may be considered include for example a hydrophilic or hydrophobic finish to the channel regions to improve the conveying of fluid and/or the fluid control of aqueous liquids.

Alternatively the film may also have an additional sealing layer which is welded onto the surface of the substrate during a hot lamination process.

Moreover, the film may be applied directly by lamination, i.e. a material joint between the film and substrate is produced without the melting on of a sealing layer by the effect of pressure and heat. The lamination may also be carried out cold preferably using an acrylate adhesive layer.

Preferably, the film is flat. However it is also possible to shape the film locally so as to form deformable chambers, for example, or to mould it in order to form pressure- or vacuum-controlled valves and microactors.

In addition to a first film, a second film may be provided on the plate-shaped substrate and/or the first film. The second film may comprise additional microfluidic structures such as channels, chambers and/or gaps. Preferably, the second film comprises structures for a biosensor, particularly measuring means such as electrical contacts and/or electrical potential surfaces and/or optical structures such as optical fibres and/or optical reflective surfaces.

For operating the microfluidic cartridge in an analyser, for example, a quantity of fluid is fed into a feed device. This may be for example a drop of blood 5 to 50 microlitres in volume, preferably 5 to 100 microlitres for lateral flow tests.

Most simply, the feed device is a fill opening. The feed device may furthermore comprise additional components. For example, the feed device may be a funnel-shaped insert which is placed in a fill opening to assist with the addition of blood and widen the filling space. The insert may be arranged in interlocking engagement on an upper plate-shaped substrate. The feed device may also comprise a finger well that surrounds a fill opening and acts as a support surface and/or positioning surface for a patient's finger during the addition of the blood.

This well is preferably provided in a plate-shaped cover element. The cover element then forms the feed device.

The device for sample separation according to the invention further comprises a separating device with means for dividing off and/or separating and/or filtering sample constituents.

The means for dividing off and/or separating and/or filtering is advantageously a membrane or a filter to which the sample liquid is supplied and wherein the liquid flows through the membrane and/or filter and wherein sample constituents are retained by the filter or the membrane.

The flow through the filter takes place through pores and/or capillaries which form an open fluid network through the filter. Advantageously, a filter made of fibreglass, polysulphone or polyethersulphone is used.

In order to separate blood plasma from a blood sample, a filter is preferably using having a mean pore size of . . . to . . . microns. Advantageously the filter is welded in an upper plate-shaped substrate in the fill opening. This cover element preferably has a recess at the fill opening into which the filter, particularly a membrane, can be inserted. Particularly preferably the membrane is welded to a surface of the recess, the attachment surface.

The flow of fluid is transported through the membrane or the filter particularly in a vertical direction of flow.

This vertical direction means that the flow is substantially perpendicular to the substrate plane of an in particular plate-shaped microfluidic metering device.

The flow thus passes through a membrane substantially in the direction of thickness.

The membrane or the filter is preferably arranged in the vertical direction between the inlet opening and an inlet chamber or collecting chamber located under the membrane/filter.

Through the capillary action of their pores or capillaries, the membrane or the filter receive and retain larger particles the size of which is greater than that of the pores or capillaries.

The pores thereby partially close up as a result of the clumping of the retained particles, so that the cross-section of flow available decreases as the separation process continues. This means there is a reduction in the flow rate of the volume flow of fluid in the microfluidic device.

On the separating device, an inlet chamber or collecting chamber is provided into which the separated sample liquid flows.

By an inlet chamber or collecting chamber is meant the space in the fluidic device which the separated sample liquid directly enters after flowing through the separating device, particularly after flowing through a filter or a membrane.

The inlet chamber or collecting chamber may be a channel and/or a chamber which is arranged directly underneath a membrane and is open at the top, so that the separated sample liquid is received by the channel and/or the chamber.

It is preferable in terms of construction if the inlet chamber or collecting chamber is formed by the space that is bounded at the top by the membrane or the filter.

The lower filter or membrane surface then forms an upper separating surface for the inlet or collecting chamber.

In this embodiment the space of the inlet chamber is bounded at the bottom by the plate-shaped substrate which forms the base of the collecting chamber. The sides of the space may be formed by walls and/or particularly preferably surrounded by a ventilating trench, as will be explained hereinafter.

The inlet chamber or collecting chamber may be totally filled by the membrane or the filter. In this embodiment, the filter or the membrane is both part of the separating device and also part of the inlet or collecting chamber.

One or more ventilating channels may proceed from the inlet chamber or collecting chamber. Moreover the design of the device is such that separated sample liquid carried out be conveyed away by one or more channels in the lateral direction.

Advantageously, the inlet chamber or collecting chamber may contain reagents which are dissolved by the stream of fluid.

Similarly, the membrane may also be soaked or impregnated with reagents such as the reagents glycine or lectin, which promote clumping of the fluid, particularly the blood, so that larger accumulations of particles are formed that are retained by the membrane. When the fluid is added, separation takes place in the membrane thus treated while at the same time a first reagent is dissolved, the first reagent affecting the biological and/or chemical and/or physical properties, particularly the viscosity of the fluid.

A second reagent may be provided in the inlet chamber or collecting chamber, which causes a detection reaction in the fluid. This may be optical staining, for example.

As the membrane or the filter has a high intrinsic capillarity, means are advantageously provided for assisting a vertical downflow of the flow volume into the adjacent inlet or collecting chamber. For this purpose the inlet or collecting chamber advantageously has one or more pillars and/or webs and/or ramp-like surfaces. These may preferably support or form the one or more notches extending in the vertical direction.

The pillars and/or webs and/or sloping surfaces are constructed such that the membrane rests on these structures. The height of the structures advantageously corresponds to the depth of the inlet or collecting chamber, the depth of which is preferably from 10 microns to 1000 microns, particularly 50 microns to 500 microns.

The notches on the structures or the structures themselves come into fluidic contact with the membrane that is to be contacted and by their capillary action convey fluid out of the membrane to the base of the chamber, so that the collecting chamber is wetted. Alternatively or additionally, the membrane may be of convex construction, the height of the convexity corresponding to the depth of the chamber, so that the membrane at the top of the convexity fits against the base of the chamber.

As the top of the membrane forms an acute angle with the base of the chamber, high capillary forces are produced there when the membrane is wetted, so that separated fluid is discharged through the gap between the membrane and the chamber base and into the collecting chamber.

Advantageously, the inlet or collecting chamber is at least partially surrounded by a trench, the depth of which is greater than that of the chamber, and which has a vent, so that the air in the inlet or collecting chamber can be displaced by the inflowing fluid through the trench. The filling trench is preferably at least 100 microns wide and at least 5 microns deep.

The volume of the inlet or collecting chamber is preferably 0.01; 0.02; 0.05; 0.1; 0.2; 0.5; 1; 2; 5; 10; 20; 50; 100; 200; 500; 1000 microlitres, while it is also possible to select chamber volumes which are obtained from adding the above values together.

The venting trench described hereinbefore forms a fluid stop, as the stream of fluid is unable to overflow the trench step. Advantageously the trench completely surrounds the inlet or collecting chamber in which the discharge channel runs, up to the outlet region of the inlet or collecting chamber, so that the air can be uniformly displaced from the inlet chamber.

In the region between the chamber outlet and the ends of the trench, which are adjacent to one another, there is a danger of an unwanted flow of fluid into the trench. There it is particularly advantageous to design the sample separation device such that there is no entry of fluid into the trench.

This is achieved on the one hand by the ends of the venting trench being widened. As a result of the widening the capillary step for filling the venting trench is enlarged, which means that the risk of accidental filling of the venting trench is significantly reduced.

The construction of the separated device according to the invention envisages that the channel for conveying the separated sample liquid from the inlet or collecting chamber is arranged at the base of the collecting chamber, i.e. the channel is formed by a recess in the base of the inlet chamber.

By the term discharge channel is meant a channel which is able to receive a liquid from the inlet chamber and convey it into a microfluidic fluid network.

The arrangement of the discharge channel in the base of the inlet chamber has the advantage that the separated sample liquid does not have to fill the inlet chamber completely to begin with in order to be carried away through a laterally positioned channel, but rather the separated sample liquid is transported away directly to analysis regions of the microfluidic cartridge.

This construction thus avoids the formation of dead volumes of sample liquid which would not be available for analysis. This is particularly advantageous in those diagnostic applications in which only a small amount of sample, such as for example a drop of blood of 10 to 50 microlitres, corresponding to a quantity of separated blood plasma volume of 5 to 20 microlitres, is available.

Moreover, the discharge channel is advantageously covered by a film in fluidtight manner at least at the points where the channel extends close to the end of the venting trench, so as to prevent an unwanted joining of the fluid between the channel and the venting trench. Advantageously, the discharge channel is also at least partly covered by the film in the inlet chamber, so as to obtain the inflow region for the separated liquid in the inlet or collecting chamber.

This covering of the channel is particularly advantageously in the form of a tongue which closes off the channel in fluidtight manner as far as the centre of the inlet or collecting chamber, so that a sample liquid introduced centrally into the fill opening and separated by the membrane can flow directly into the central discharge channel.

In a preferred embodiment of the invention, the channel has means for assisting the capillary wetting of the channel.

These means may advantageously be a notch with an increased capillary action that connects the base of the chamber to the base of the discharge channel.

As another alternative means there may be at least one ramp between the base of the chamber and the base of the channel, which has a connecting capillary action in the same way.

The invention is described in more detail in the following embodiments by way of example, wherein.

Figure 1:
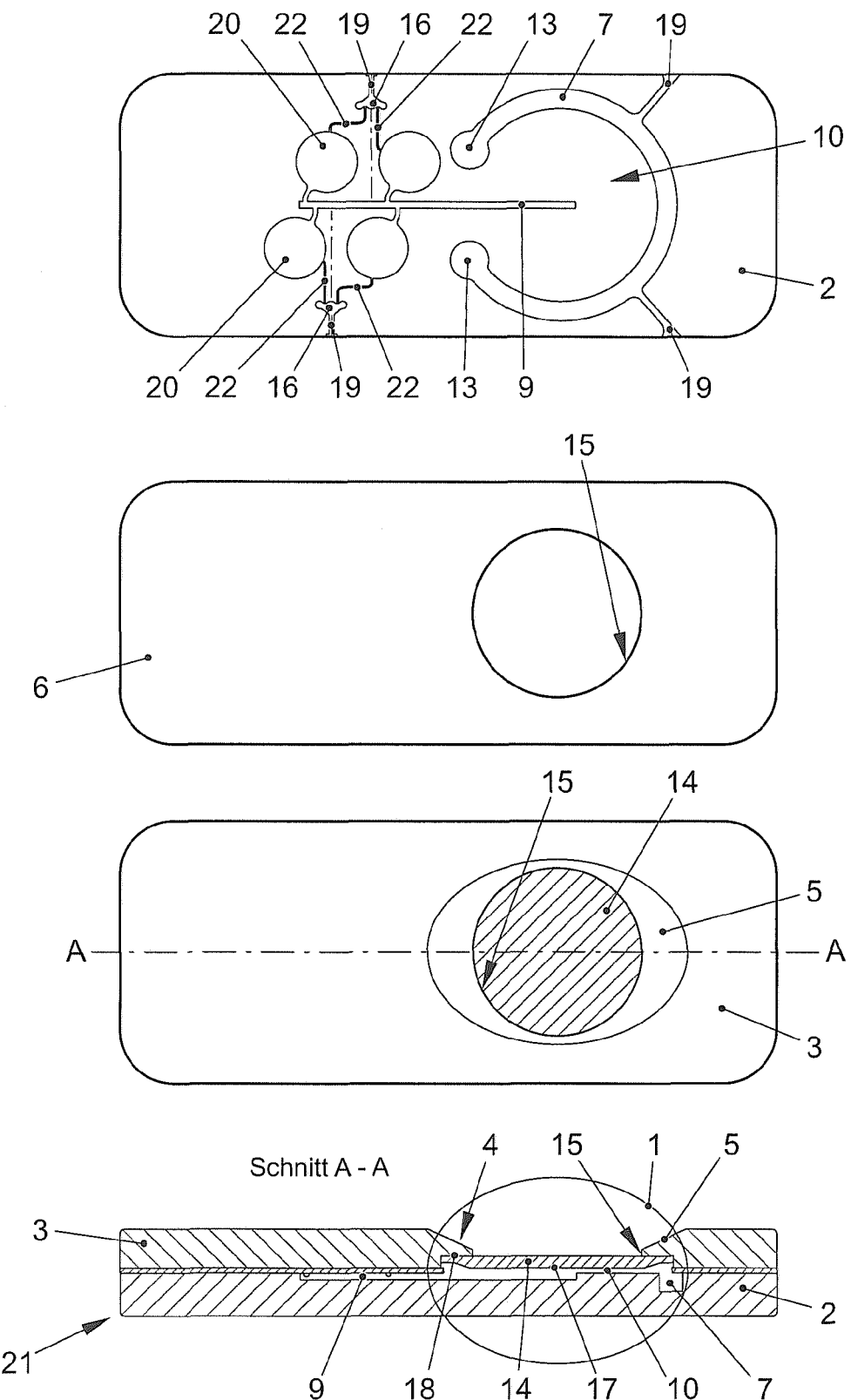
FIG. 1 shows a first embodiment of a cartridge (21) with a device for sample separation (1)

A cartridge (21) having a device for sample separation (1) according to the invention is shown in FIG. 1. The cartridge (21) is assembled from a number of components (2, 3, 6). The base of the cartridge (21) forms a lower plate-shaped substrate (2) in which microfluidic structures are moulded, having widths ranging from a few microns to several millimetres.

The lower plate-shaped substrate (2) is a plastic plate, in particular, and comprises a sample feed region. The sample feed region is, more particularly, an inlet chamber (10) into which a sample liquid that is to be separated flows after the separation.

The inlet chamber (10) is at least partially bounded by a venting trench (7). The venting trench (7) consists of a preferably deepened channel with a width of at least 100 microns and a depth of at least 5 microns. The venting trench (7) forms a capillary step to the inlet chamber (10) and is vented through venting channels (19), so that the liquid flowing into the inlet chamber is able to displace the air in the inlet chamber (10) through the trench (7) and the channels (19) and the separated sample liquid itself stops at the edge of the trench (7).

As shown in the lower diagrammatic assembled view in FIG. 1 and FIGS. 7 to 10, the welding of the membrane (14) into the upper plate-shaped substrate (3) along the attachment surface (18) forms an encircling gap (25) which extends over both the feed channel (9) and the venting trench (7).

The gap or annular channel (26) produced by the edge of the membrane extends coincidentally over the venting trench (7) and is covered by the film (6) at the channel region.

The fill opening (15) in the film substantially corresponds, particularly preferably, to the diameter of the membrane (14) in the unsecured region of the membrane, so that the edge of the foil rests on the circumference of the membrane surface. As very thin films 20 to 200 microns thick are used which are elastic, the film (6) is stabilised by resting on the membrane (14) and prevents an unwanted flow of fluid into the gap (25).

Particularly advantageously, the end of the encircling venting trench (7) of the inlet chamber (10) is widened. This widening (13) of the trench performs the task of preventing a flow of fluid from the inlet chamber (10) or the discharge channel (9) into the venting trench (7).

The trench widening (13) helps to ensure that there is no undesirable flow of fluid from the channel (9) through the gap (25) or from the membrane (14) through the gap (25) into the venting trench (7) as a result of capillary vertical or three-dimensional wetting. The widening increases the capillary resistance for an unwanted capillary wetting of the venting trench, as the distance between the said gap (25) and/or the membrane (14) from the bottom of the venting trench is increased.

Alternatively or in an assisting capacity it may advantageously be envisaged that a hydrophobically acting film (6) at least partially covers the venting trench.

Figure 7:
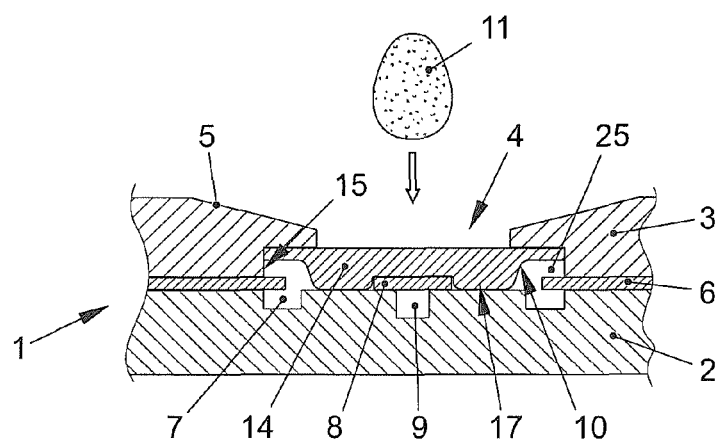
FIGS. 7 to 9 show a cross-section through the sample separation (1) according to FIGS. 2, 3 and 6 when a sample liquid is added.
Figure 8:
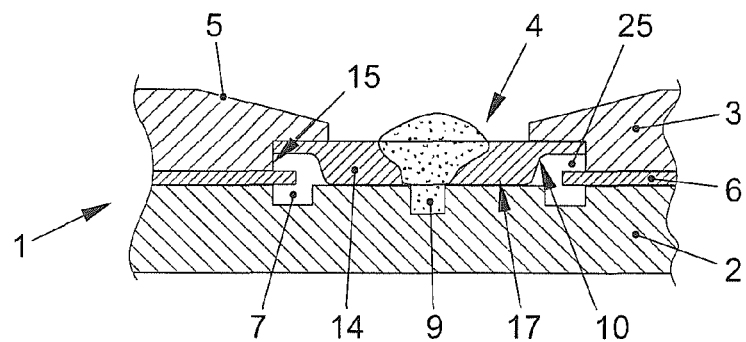
Figure 9:
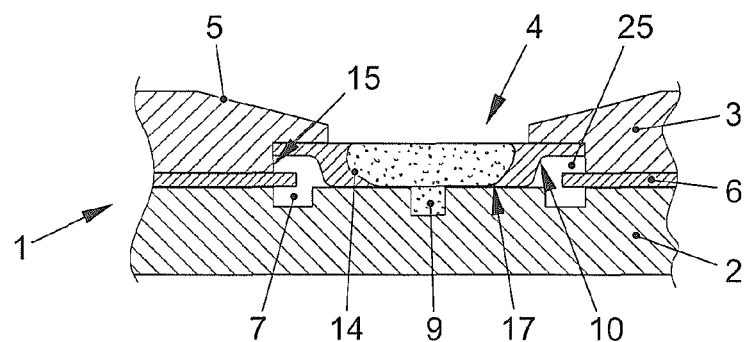

FIGS. 7 to 9 show a partial covering of the encircling venting trench (7) of this kind, the film (6) extending approximately to the centre of the venting trench (7). This ensures that on the one hand the venting function of the trench (7) is maintained but on the other hand no aqueous liquid gets into the gap (25) or passes from the gap (25) into the venting trench (7), and that it is driven back by the hydrophobic film (6) which is difficult to wet.

Particularly advantageously the film (6) is constructed so as to seal off and/or cover the discharge channel (9) close to the ends of the venting trench (7) in fluidtight manner.

This covering may be a tongue (8) which is formed in one piece with the film and projects into a fill opening (15) in the film (6), as schematically shown in FIGS. 2, 3, 4, 6 and 7.

The novel construction according to the first embodiment allows the inlet chamber (10) to be filled completely, while functionally it is preferable not to fill the inlet chamber (10) completely but to discharge the separated volume of sample directly through the discharge channel (9) for further reaction and analysis.

The discharge channel (9) conveys the separated sample liquid into a fluidic network, particularly a capillary network consisting of analysis chambers (20) and other components.

In an embodiment according to FIG. 1, at least one, and in this embodiment four, analysis chambers (20) are fluidically connected to the channel (9). The analysis chambers (20) may be filled either sequentially or in parallel.

Thus, parallel or sequential filling may be carried out through active or passive valves (not shown) for controlling the flow or through controlled venting.

The analysis chambers (20) are connected to capillary stops (16) through other channels. In operation, separated sample liquid first enters an analysis chamber (20), displaces the air enclosed in the analysis chamber (20), fills the chamber (20) completely, with no air bubbles, and then flows into a first venting channel (22).

The first venting channel (22) is then filled with fluid. The fluid uptake by the first venting channel (22) ensures that the analysis chamber (20) is completely full.

This therefore ensures that there are no air bubbles remaining in an analysis chamber (20). Air bubbles may interfere with or falsify the diagnostic analysis.

This may occur for example if reagents are not dissolved in the analysis chamber, as regions of the chamber underneath an air bubble are not wetted.

Moreover, total filling ensures that a defined sample volume, namely the volume of an analysis chamber (20), reacts with the reagents, particularly detection bodies, and thus a qualitative and quantitative analysis value can be obtained.

As the sample liquid in the first venting channels (22) does not contribute to the analysis reaction, i.e. is not a useful volume but a dead volume, the volume proportion of the first venting channels should make up at most 5% of the total volume of the analysis chambers (20).

According to the first embodiment shown in FIG. 1, it is envisaged that two first venting channels (22) end in a capillary stop (16), thereby interrupting the fluid flow of the sample liquid.

Advantageously, the capillary stop (16) is constructed so that the venting channel (22) has a smaller cross-sectional area than the capillary stop (16).

The venting channel (22) and the capillary stop (16) share a common separating surface, namely the upper separating surface, which is bounded by the underside of the film (6). Typically, film material or the adhesive layer of a film are hydrophobic, so that the capillary flow along the underside of the film, corresponding to the upper side of the channel (22), is made difficult.

Preferably, the capillary stop (16) is deeper and wider in construction than the first venting channel (22).

As a result, geometric capillary steps are produced both in the lateral directions and in a vertical direction.

Particularly advantageously, the film (6) may have recesses, at least at the capillary stop (16), such that at the end of the first venting trench the capillary stop (16) extends into the film (6).

Compared with the two side surfaces of the channel (22) the capillary stop (16) is thus wider and compare with the floor and ceiling surfaces of the channel (22) it is also deeper and higher.

As a result, capillary steps are present in this particularly preferred embodiment both in all the lateral directions and also in all the vertical directions.

The capillary stop (16) is vented by another venting trench (19) which fluidically connects the capillary stop (16) to a side face of the cartridge (21).

Because the channel recesses (9) and chamber recesses (20) are provided with a covering surface by the film, three-dimensional full-volume fluid wetting is achieved. To assist this, the film (6) and/or the recesses (9, 22, 20) may be made at least partly hydrophilic, in particular in the form of a coating of a hydrophilic fluid applied thereto which is then dried on.

The film (6) and/or the structures (7, 10, 13, 16, 19) may advantageously also be made locally hydrophobic.

The venting channel (7) and its widened portion (13) are preferably made totally hydrophobic so as to reduce the possibility of capillary wetting of the trench (7) and its widened portion (13) by an aqueous liquid.

The base of the fill region (10) may be made locally hydrophobic, particularly in the region of the venting trench (7), to prevent aqueous sample liquid from transferring into the trench (7).

In particular the capillary stop (16) is advantageously made totally hydrophobic, so as to improve the capillary stopping and/or retaining function of the capillary stop.

As the film (6) covers these structures, it is advantageously provided with a hydrophobic coating in these functional areas.

This may be done for example by locally printing the film with a hydrophobic coating in these partial regions.

The local coating, particularly spotting, with hydrophilic coatings is preferably provided in fluid-carrying regions such as the discharge channel (9), the analysis chambers (20) and the first venting channel (22).

A coating with a hydrophobic or hydrophilic film functionally contributes in these regions to an improved and advantageously complete filling of these structures (9, 20, 22) substantially free from air bubbles.

The film is provided at least locally with an adhesive layer, particularly a layer of glue. Preferably, the two film surfaces are provided with an adhesive coating over at least part of their surface, so that the film can be used to join both the cartridge base (2) and the cover element (3).

In the joining process, first of all a first cover film is removed from the film (6), so as to expose a first adhesive coating. Then the cartridge base (2) and the film (6) are positioned relative to one another and adhered at the exposed adhesive surface.

After the adhesion, a second cover film is removed from the film (6), the cartridge base (2) with adhesive applied is positioned relative to the cover element (3) and the cartridge base (2) is joined to the cover element (2) by means of the film (6).

First of all the membrane (14) is welded into the centre of the cover element (3).

The product obtained is the cartridge (21) as shown at the bottom of FIG. 1, comprising a separating device (1) according to the present invention.

As an alternative to the double-sided adhesive film used, it is possible to use a film (6) with no adhesive layer. This may advantageously be a film (6) which has a sealing layer at least locally on one side.

In the manufacture of the cartridge the film (6) is laminated on by means of the sealing layer. For this, the film with the sealing layer is positioned on the cartridge base (2), the sealing layer is welded on thermally and a fluidtight connection is made between the cartridge base (2) and the film (6).

Alternatively, the film may also be applied in particular by a cold lamination process, in which in particular an acrylate adhesive layer is used to form the bond.

When a laminating foil (6) is used the cover element may advantageously be welded on, attached to the cartridge base by riveting or another double-sided adhesive film may be provided for securing the cover element to the laminating film.

Advantageously, the cover element comprises a well (5). This assists with the addition of sample liquid, thanks to its funnel shape, it holds the fluid in the well region and conveys it to the fill opening (15).

Particularly advantageously, the well (5) is moulded approximately up to the attachment surface (18); in particular the funnel depth of the well (5) corresponds substantially to the vertical distance between the attachment surface (18), the membrane (14) and the surface of the cover element (3).

This design of the well (5) ensures a direct flow of the sample fluid applied to the well surface into the membrane region.

The funnel depth is advantageously from 0.5 millimetres to 10 millimetres.

Particularly advantageously, the well is circular or elliptical, the radius of the long side of the in particular elliptical well (5) being 1 to 1.5 centimetres and the radius of the short side being 0.7 to 1 centimetre.

The radius of a circular well (5) should be, in particular, 1 to 1.5 centimetres.

Figure 2:
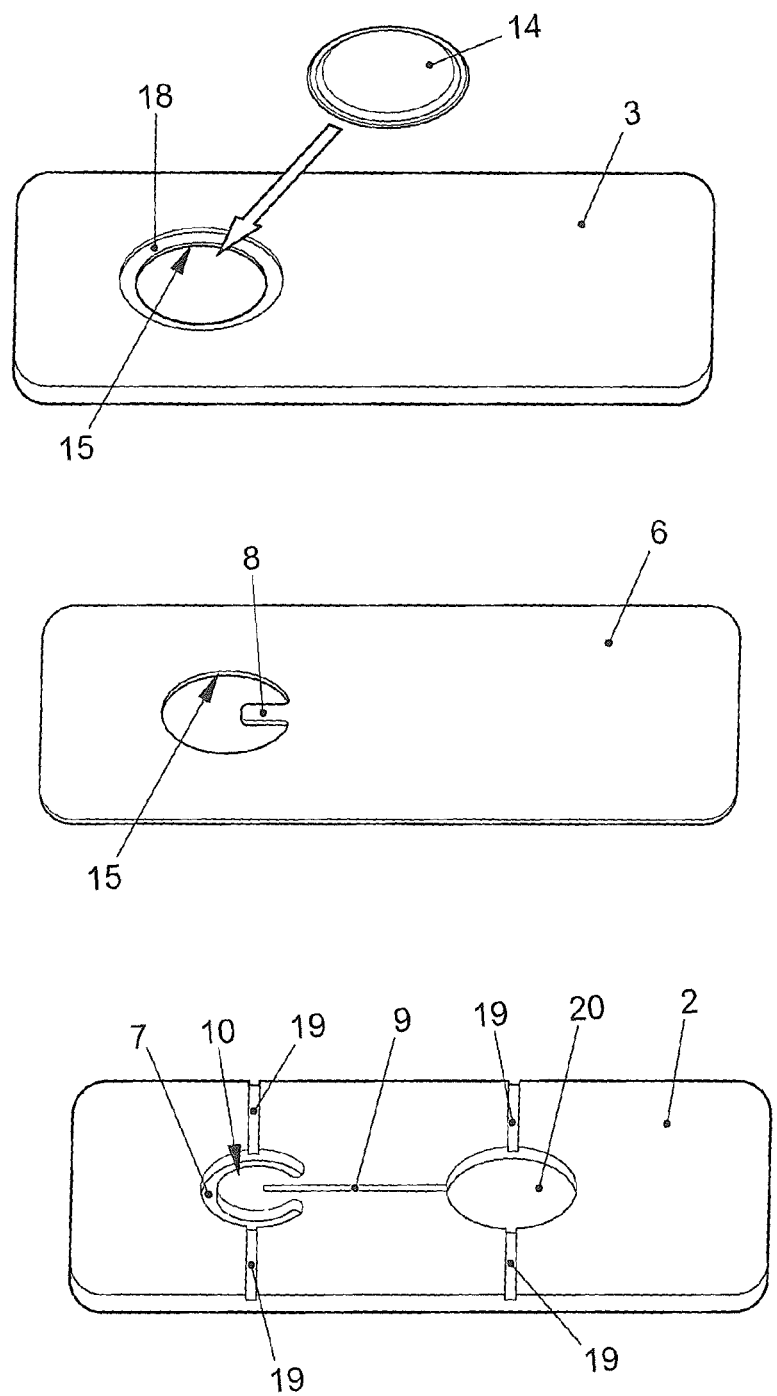
FIG. 2 shows a second embodiment of a cartridge (21) with a device for sample separation (1)
Figure 3:
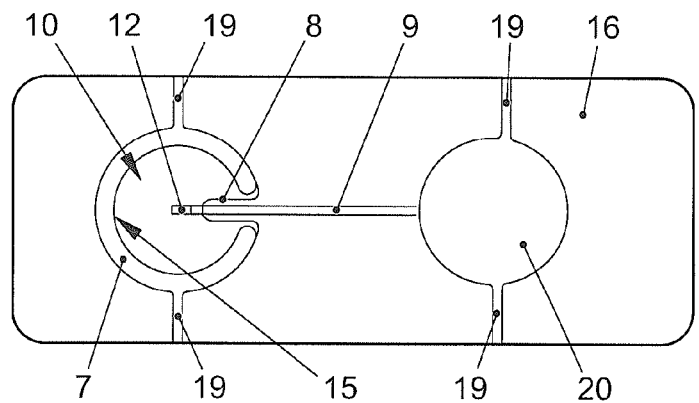
FIG. 3 shows a view of the cartridge (21) according to FIG. 2 with cover film (6)

In another second embodiment according to FIG. 2, the lower plate-shaped substrate (2), the base of the cartridge (21) comprises a fluidic network consists of a discharge channel (9) and an analysis chamber (20) vented through channels (13). The channel (9) receives separated sample fluid centrally from an inlet chamber (10). The inlet chamber (10) is vented by means of an encircling trench through channels (19).

In the second embodiment according to FIG. 2 the upper plate-shaped substrate (3), the cover element (3), is shown with the underside.

The cover element (3) comprises, around the fill opening (15), a recess with an attachment surface (18). A membrane (14) is inserted in the centre of this recess and in particular is thermally attached to the attachment surface (18).

The film (6) is a laminating film which is laminated onto the lower plate-shaped substrate (2).

After the attachment of the membrane (14) to the recess of the upper plate-shaped substrate (3), this cover element is positioned with the separating region towards the fill opening (15) in the film and is adhered to the film.

Instead of adhesion, alternative attachment processes such as ultrasonic welding or riveting may be used.

It would also be possible to secure or clamp the components to one another by means of another external housing (not shown), for example using depressing and/or positioning means and/or elastic retaining means in the external housing.

The film (6) comprises a fill opening (15) into which a tongue-shaped film portion projects.

FIG. 7 shows a cross-section through a sample separation thus attached. FIG. 7 is a cross-section level with the tongue (8).

As can be seen from FIG. 7 relating to the second embodiment, the tongue (8) covers the channel (9) in the outer region of the inlet chamber (10), so that in the outer region of the inlet chamber (10) there is no inflow of sample liquid from the inlet chamber (20) into the channel (9).

In the attached state, the membrane (14) rests at least partly on the tongue (8).

In the embodiment according to FIGS. 7 to 9, the membrane (14) advantageously fills completely. The membrane rests on the covering (8) and the base of the inlet chamber (10), so that the membrane (14) encloses the cover (8). Particularly advantageously, the inlet chamber (10) is almost completely filled by the membrane (14), so that the dead volume in the chamber is approaching zero.

By the dead volume of the inlet chamber is meant the volume in the inlet chamber that is present between the lower separating surface of the membrane (14), the separating surface (17) and the base of the inlet chamber and has a capillary effect on the fluid. This capillary effect is produced in particular by gaps left between the membrane (14) and the base of the inlet chamber and is able to hold back fluid in the inlet chamber undesirably by its capillary action.

The volume of the membrane (14) may also produce dead volumes at least partly as a result of the inherent capillary network, as sample liquid is held back by capillary action in the capillary channels and capillary pores of the membrane (14).

As schematically shown in FIGS. 8 and 9, the membrane (14) is located in the opening region of the central channel (9), preferably over the entire surface of the base of the inlet chamber (10).

For sample separation, a sample is placed in the feed device (4). According to FIGS. 7 to 9 this is a drop of blood.

FIGS. 8 and 9 are sections through the sample separation (1) in the central region of the inlet chamber (10).

As can be seen from FIG. 8, the drop of blood is received by the capillary membrane (14), while larger solid blood particles are deposited in the membrane.

As a result of the hydrostatic fluid pressure of the sample liquid, a fluid drop of separated sample liquid, in this case blood plasma, is formed in the membrane, particularly centrally in the inlet chamber.

The shape and length of the covering (8), particularly the film tongue (9), is selected in particular so that in the central region of the inlet chamber (10) the channel (9) is not covered but is open at the top. The upper separating surface of the channel (9) is advantageously formed by the underside of the membrane (14). In this way a central opening region of the channel (9) with a small fluid aperture is obtained.

As shown in FIGS. 8 and 9, it is possible for the separated sample liquid, the blood plasma, to be received directly by this channel opening.

The plasma thus flows from the separation membrane (14) through the inlet chamber (10) into the opening of the channel (9) without totally filling the fill chamber (10) during the separation.

Functionally, this has the effect that the plasma that is to be analysed is fed directly to the analysis chamber (20). This direct feeding thus contributes to a short analysis time for an assay, for example, as fluid filling times are shortened.

Another functional effect of the partial covering of the channel is the reduced dead volume of the membrane (14), as in this arrangement the fluid can flow directly into the channel (9) without the membrane (14) having to be totally wetted.

With a reduced dead volume there is thus a larger amount of sample volume available, in this case blood plasma.

In investigations of finger-prick blood samples, in particular, i.e. 1 to 50 microlitres of blood, the separation quantity is a critical amount for diagnostic tests, as after the separation often only 5 to 20 microlitres of plasma are available for antibody reactions, for example.

Figure 4:
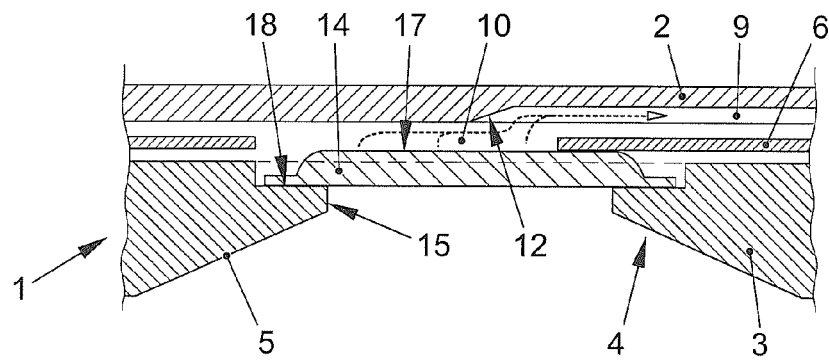
FIG. 4 is a sectional view of the sample separation (1) of a cartridge according to FIGS. 2 and 3

FIG. 4 shows a sample separation (1) of this kind in longitudinal section, the filling region pointing downwards.

The film (6) at least partially covers a discharge channel (9), so as to leave a central opening of the channel (9).

Particularly advantageously, the opening region of the channel (9), in this case the channel end, is provided with means for conveying the fluid from the chamber into the channel. Particularly preferably, the means is a notch, a transition profile and, more particularly, a ramp. This ramp (12) decreases the capillary resistance between the channel (9) and the base of the inlet chamber (10), so that the wetting of the channel and the flow of liquid into the channel are improved.

In FIG. 4, the fluid flows of plasma from the membrane (10) through the fill chamber (10) into the channel (9) are represented by arrows.

Separated sample liquid, i.e. blood plasma in this embodiment, can be transported into the channel (9) from outer regions of the inlet chamber as well. This can be achieved, for example, if the channel has a higher capillarity than the inlet chamber (10), or if the plasma is conveyed by the application of excess pressure (from outside) and/or reduced pressure (on the channel (9)) through the sample separation (1) into the channel (9) and the further fluidic network.

Figure 5:
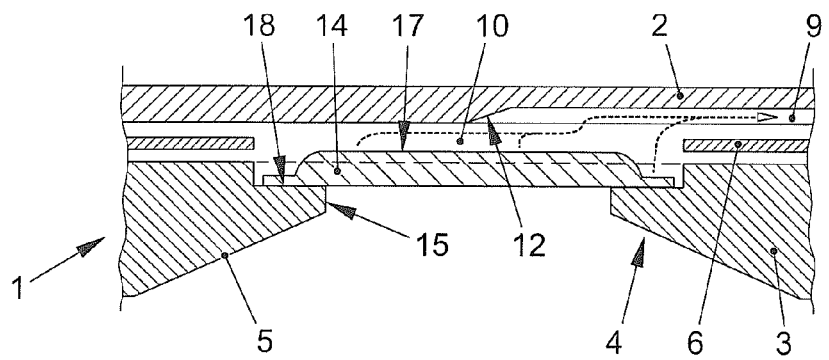
FIG. 5 is a sectional view of the sample separation (1) of a cartridge according to FIG. 1

FIG. 5 shows a sample separation according to the first embodiment in FIG. 1 in longitudinal section.

According to this first embodiment, the channel (9) is open throughout the entire fill chamber (10) and receives liquid all along its length in the fill chamber.

Figure 6:
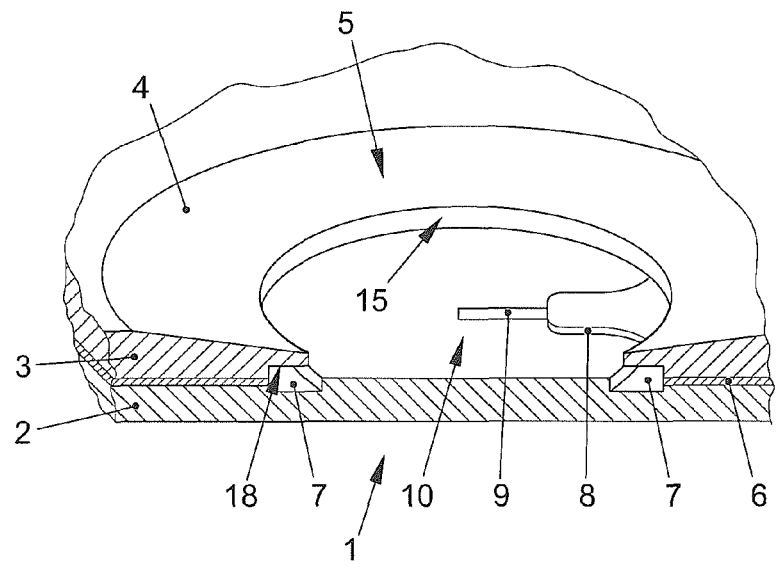
FIG. 6 is a perspective view of the sample separation (1) according to FIGS. 2 and 3

A perspective view of a sample separation 1 according to the invention is shown in FIG. 6. The membrane (14) is not shown, to make it possible to see into the inlet chamber (10).

In terms of construction, this embodiment substantially corresponds to the embodiment in FIGS. 2, 4 and 7 to 9.

LIST OF REFERENCE NUMERALS

1—sample separation
2—lower plate-shaped substrate
3—upper plate-shaped substrate
4—feed device
5—well
6—film
7—venting trench
8—channel cover
9—channel
10—collecting chamber
11—sample
12—ramp
13—trench widening
14—membrane
15—fill opening
16—capillary stop
17—separating surface
18—attachment surface
19—venting channel
20—analysis chamber
21—cartridge
22—first venting channel
25—gap

The invention claimed is:

1. A device for plasma separation comprising a feed device for vertically receiving a sample, a separating device for separating sample constituents, an inlet chamber for receiving separated sample liquid, said inlet chamber being almost completely filled by the separating device, so that the dead volume in said inlet chamber approaches zero, and a channel which conveys the separated sample liquid in the lateral direction from the inlet chamber, characterised in that the channel is formed by a recess in the base of the inlet chamber, wherein apart from a region in which the channel run, the inlet chamber is surrounded by a venting trench which forms a capillary stop for sample liquid and laterally bounds the inlet chamber, wherein the channel is partly covered by a film, wherein the film comprises a tongue which is connected in one piece to the film and wherein the tongue projects into a fill opening in the film, wherein the tongue covers the channel in an outer region of the inlet chamber, so that in the outer region of the inlet chamber there is no inflow of sample liquid from the inlet chamber into the channel, wherein the shape and length of the tongue is selected so that in a central region of the inlet chamber the channel is not covered but is open at a top region thereof forming an inflow region for receiving the separated sample liquid in the channel, wherein the inflow region is located substantially in the centre of the inlet chamber, wherein the tongue-covered portion of the channel is operable to provide three-dimensional full-volume fluid wetting of the channel.

2. The device for plasma separation according to claim 1, characterised in that the separating device has a vertical fill opening and a membrane, wherein a surface of the membrane forms a separating surface between the separating device and the inlet chamber and the inflow region for the separated sample liquid is positioned under the separating surface to directly receive sample liquid separated by the separating device wherein the inflow region is configured to be wetted directly by the sample liquid and the tongue-covered portion of the channel is operable to facilitate flow of separated sample liquid into the channel.

3. The device for plasma separation according to claim 1, characterised in that the channel comprises means for discharging a fluid, so that fluid flows from the base of the chamber, particularly over the means for discharging a fluid, into the channel.

4. The device for plasma separation according to claim 1, characterised in that the feed device comprises a well which is formed in an upper plate-shaped substrate.

5. The device for plasma separation according to claim 1, characterised in that the feed device comprises an insert which is arranged in interlocking engagement on an upper plate-shaped substrate.

6. The device for plasma separation according to claim 2, characterised in that the separating surface in the region of a channel opening abuts the base of the inlet chamber.

7. The device for plasma separation according to claim 1, characterised in that the venting trench comprises widened portions at its ends.

8. The device for plasma separation according to claim 1, characterised in that on an upper plate-shaped substrate at the fill opening is provided a recess which comprises an attachment surface for a membrane.

9. The device for plasma separation according to claim 1, characterised in that the tongue rests in fluidtight manner on the channel.

10. The device for plasma separation according to claim 1, characterised in that the film has at least one adhesive layer.

11. The device for plasma separation according to claim 1, characterised in that the film at least partly covers a venting trench.

12. A device for plasma separation comprising a feed device for vertically receiving a sample, a separating device comprising a vertical fill opening and a membrane for separating sample constituents, an inlet chamber for receiving separated sample liquid, said inlet chamber being almost completely filled by the separating device, so that the dead volume in said inlet chamber approaches zero, wherein a surface of the membrane forms a separating surface between the vertical fill opening and the inlet chamber and the inlet chamber is positioned to receive fluids from the separating device, and a channel which conveys the separated sample liquid in a lateral direction from the inlet chamber, wherein the channel is formed by a recess in the base of the inlet chamber, wherein apart from a region in which the channel runs, the inlet chamber is surrounded by a venting trench which forms a capillary stop for sample liquid and laterally bounds the inlet chamber, wherein the channel is partly covered by a film, the film comprising a tongue which projects into a fill opening in the film, wherein the tongue covers the channel in an outer region of the inlet chamber, so that in the outer region of the inlet chamber there is no inflow of sample liquid from the inlet chamber into the channel, wherein the shape and length of the tongue is selected so that in a central region of the inlet chamber the channel is not covered but is open at a top region thereof forming an inflow region located substantially in the centre of the inlet chamber and positioned under the separating surface to directly receive separated sample liquid in the channel, wherein the inflow region is configured to be wetted directly by the sample liquid and the tongue-covered portion of the channel is operable to provide three-dimensional full-volume fluid wetting of the channel and the inflow region is operable to facilitate flow of separated sample liquid into the channel.

* * * * *